United States Patent
Kim et al.

(10) Patent No.: US 9,983,111 B2
(45) Date of Patent: May 29, 2018

(54) LOW PROFILE SHEAR-SENSING UNIT

(71) Applicant: THE REGENTS OF THE UNIVERSITY OF CALIFORNIA, Oakland, CA (US)

(72) Inventors: Chang-Jin Kim, Beverly Hills, CA (US); Muchen Xu, Los Angeles, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days. days.

(21) Appl. No.: 15/356,062

(22) Filed: Nov. 18, 2016

(65) Prior Publication Data

US 2017/0146439 A1    May 25, 2017

Related U.S. Application Data (60) Provisional application No. 62/258,344, filed on Nov. 20, 2015.

(51) Int. Cl.
*G01L 1/22* (2006.01)
*G01N 13/02* (2006.01)

(52) U.S. Cl.
CPC ..... *G01N 13/02* (2013.01); *G01N 2013/0216* (2013.01)

(58) Field of Classification Search
CPC ............... G01N 2013/0216; G01N 13/02
USPC ..................................... 73/862.627
See application file for complete search history.

(56) References Cited

U.S. PATENT DOCUMENTS

| | | | | |
|---|---|---|---|---|
| 4,896,098 A | * | 1/1990 | Haritonidis | G01N 13/00 324/663 |
| 5,199,298 A | * | 4/1993 | Ng | B81C 1/00158 73/147 |
| 6,341,532 B1 | * | 1/2002 | Xu | G01L 1/148 73/147 |
| 6,467,761 B1 | | 10/2002 | Amatucci et al. | |
| 7,921,731 B2 | | 4/2011 | Bajikar et al. | |
| 8,833,175 B2 | | 9/2014 | Chandrasekharan et al. | |
| 8,879,052 B2 | | 11/2014 | Horowitz et al. | |

(Continued)

OTHER PUBLICATIONS

Bao, Xiaoqi et al., Sensor for direct measurement of the boundary shear stress in fluid flow, Proc. of SPIE vol. 7981 79814G-1-79814G-8 (2011).

(Continued)

*Primary Examiner* — Max Noori
(74) *Attorney, Agent, or Firm* — Vista IP Law Group LLP (57) ABSTRACT

A low-profile shear-sensing unit includes a floating plate surrounded by a frame and a displacement sensor that measures in-plane movement of the floating plate. Covered with a surface sample, the floating plate is displaced by the friction drag (i.e., shear) on the surface caused by the flow of fluid and the in-plane displacement is measured by the displacement sensor. The shear force on the sample surface is then obtained by multiplying the measured displacement and the spring constant of the flexure beams, which suspend the floating plate. The floating plate and the flexure beams are formed out of one plate or substrate to achieve monolithic construction with a beam geometry that leads to a high-resolution measurement.

21 Claims, 8 Drawing Sheets

(56) References Cited

U.S. PATENT DOCUMENTS

2013/0276518 A1* 10/2013 Dagalakis .............. G01N 11/16
                                                                                                   73/54.25

OTHER PUBLICATIONS

Schlichting, Hermann, Boundary-Layer Theory, pp. 638-639 (McGraw-Hill, 1979).
Schetz, Joseph A., Direct Measurement of Skin Friction in Complex Flows, 48th AIAA Aerospace Sciences Meeting Including the New Horizons Forum and Aerospace Exposition Jan. 4-7, 2010, Orlando, Florida (28pages).
Sheplak, Mark et al., MEMS Shear Stress Sensors: Promise and Progress,24th AIAA Aerodynamic Measurement Technology and Ground Testing Conference, Portland, OR Jun. 28-Jul. 1, 2004.

* cited by examiner

FIG. 6

LOW PROFILE SHEAR-SENSING UNIT

RELATED APPLICATION

This Application claims priority to U.S. Provisional Patent Application No. 62/258,344 filed on Nov. 20, 2015, which is hereby incorporated by reference in its entirety. Priority is claimed pursuant to 35 U.S.C. § 119 and any other applicable statute.

STATEMENT REGARDING FEDERALLY SPONSORED RESEARCH AND DEVELOPMENT

This invention was made with Government support under 1336966, awarded by the National Science Foundation, and HR0011-15-2-0021, awarded by the U.S. Department of Defense, Defense Advanced Research Projects Agency. The Government has certain rights in the invention.

TECHNICAL FIELD

The technical field generally relates to devices used to measure shear forces and, more particularly, devices used to evaluate and measure the skin friction of surface samples in fluid flow.

BACKGROUND

Shear stress or skin friction measurement is a crucial topic in fluid mechanics. It not only provides insights into complex flow phenomena which help the design of watercraft or aircraft, but also may serve as a feedback for flow-control. There are two broad classes of methods for shear stress measurement: indirect measurement and direct measurement. Indirect measure methods usually rely on theoretical models and associated assumptions, which are inaccurate if the flow is complex. Direct measurement methods do not require prior knowledge of the flow conditions and usually employ a floating element, which displaces due to shear stress.

Among the direct measurement methods, micro-electro-mechanical-systems (MEMS)-based shear stress sensors are promising for shear stress measurement because of its compactness, monolithic structure, high sensitivity and accuracy, and high spatial and temporal resolution. However, one cannot obtain the floating element of a wide range of sizes (e.g., tens of centimeters in length) because the fabrication is limited by the size of silicon wafer used for MEMS fabrication. Also, changing sizes of the floating element requires a new set of photolithography masks. Overall, MEMS devices are too expensive for small-batch and customized orders. Moreover, MEMS sensors are usually not robust when subject to water or particle impingement; and are thus constrained by the packaging technique. Also, MEMS devices usually use silicon, which is brittle and easily broken when sample surfaces are frequently mounted thereon.

Among the direct measurement methods, the single-pivot shear stress sensor is a well-known design commonly used in practice. Unlike MEMS sensor and this invention, the single-pivot shear stress sensor is usually assembled of parts instead of monolithically fabricated. The need to assemble the device increases the chance of floating element misalignment and also increases the cost. However, it is made mostly of metals and robust for experimentation and handling. A shear sensor of a direct measurement type made of a tough material such as a metal (as opposed to a brittle material like silicon) yet based on monolithic construction for high performance is highly desired. A key feature of the shear sensing unit in this invention is the relatively large floating element with microscale features made monolithically of a non-brittle material.

BRIEF DESCRIPTION OF THE DRAWINGS

FIG. 2A illustrates a top view of a schematic representation of a shear-sensing unit embodiment of FIG. 1. FIG. 2A is not drawn to scale; the beams and gaps are much longer and thinner in reality than appearing in the FIG. 2A.

FIG. 2B illustrates a cross-sectional view of a schematic representation of a shear-sensing unit embodiment of FIG. 1 taken along the line A-A' of FIG. 2A. FIG. 2B is not drawn to scale; the middle plate (i.e., floating plate) is much larger in the in-plane direction than it appears in FIG. 2B.

SUMMARY

In one embodiment, the invention pertains to a low-profile shear-sensing unit, which facilitates evaluation of different surface samples for their respective skin frictions in fluid flow. The shear-sensing unit is designed to be useful for a wide range of application conditions, encompassing not only laboratory tests but also field tests. The sensing unit includes a floating plate located within a frame that is machined from a monolithic substrate to physically respond to a shear force applied by a fluid and a displacement sensor that reads the response. Covered with a surface sample to be tested, the floating plate located in the sensing unit is displaced by the friction drag (i.e., shear) on the sample surface by the flow, and the displacement is measured by the encoder of the displacement sensor. The shear force on the sample surface is then obtained by multiplying the measured displacement and the spring constant of the flexure beams which suspend the floating plate in the frame. The floating plate and the flexure beams are carved out of or otherwise formed from one plate to achieve a monolithic construction, which ensures reliable and precise response. The plate-type mechanism helps make the unit low profile, so that the unit is useful for many different application conditions. The application region (e.g., boat hull, airplane wing) does not need to be modified much to apply this low-profile unit for an experimental study.

In contrast with the existing sensors that also employ a floating plate suspended by flexure beams, the low-profile shear-sensing unit uses very narrow and long but relatively thick beams that make the spring (i.e., the flexure beams) highly flexible to the flow direction but rigid to all other directions. This robust design also allows the floating plate to be large (i.e., of a large area), leading to the high resolution sensing (e.g., resolution smaller than 100 μN) and convenient usage. Among the displacement sensing methods available, optical sensing, which can be used in connection with the sensing unit described herein in one or more embodiments is often advantageous over other methods. Compared with a strain gauge, which is commonly used in floating element shear stress sensors, the optical-based method is not sensitive to temperature variations and can be used at high temperatures if an optical fiber is used (keeping the electronics remote or external to the sensing element). Compared with the capacitance sensing method, the optical method is immune to electromagnetic interference and can be applied to a wide variety of fluids.

While most of the existing shear sensors focus on the shear on smooth surfaces, there is also a need to measure the shear stress on other customized surfaces, such as superhydrophobic surfaces, rough surfaces, polymer-releasing surfaces, anti-fouling surfaces, etc. Different from other direct shear stress sensors, the disclosed shear-sensing unit is designed to allow users to repeatedly attach and detach different surface samples on the shear-sensing unit while retaining high sensitivity and accuracy. Typically fabricated by a slit-cutting method such as wire electrical discharge machining (EDM), although other methods such as casting or molding are also possible, this sensing unit allows customizing sensor parameters (e.g., plate size, beam size) with low cost and efforts to meet different needs. The slit-cutting method, such as wire EDM, allows manufacturing multiple sensing plates stacked together at the same time for mass manufacturing. It also allows a wide choice of materials for different applications (e.g., anti-corrosion, high temperature). Not requiring much space under the surface of a testing object, the low-profile unit may be applied to many field conditions (e.g., on the boat hull, on the aircraft wing) as well as the usual lab conditions involving water or air tunnels. Utility of the cutting paths and sequences described herein to make highly flexible beams necessary for the high-sensitivity sensing unit has been proven with wire EDM, but the same technique could also be used for other machining methods (e.g., waterjet cutting) when extremely flexible parts are required. It will be difficult to obtain the high precision machining with other fabrication methods such as casting or molding, but they can be practical for large volume production.

In one embodiment of the invention, a shear-sensing unit includes a frame plate; a floating plate disposed inside the frame plate in substantially the same plane with the frame plate and secured to the frame plate via a plurality of flexure beams disposed in substantially the same plane with the frame plate, the floating plate having a sample supporting surface and a back surface; a ruler secured to or formed on the back surface of the floating plate; and a displacement sensor configured to sense in-plane movement of the ruler. The plurality of flexure beams are shaped to deform in a direction along a plane of the floating plate and wherein each of the plurality of flexure beams has a width smaller than 1 mm, a thickness larger than the width, and total length at least fifty (50) times larger than the width.

In another embodiment of the invention, a method of using the shear-sensing unit described above includes mounting a sample on the sample supporting surface; subjecting the sample on the shear-sensing unit to fluid flow over the sample; measuring the displacement of the ruler; and converting the measured displacement to a measured shear force on the floating plate.

DETAILED DESCRIPTION OF ILLUSTRATED EMBODIMENTS

Figure 1A:
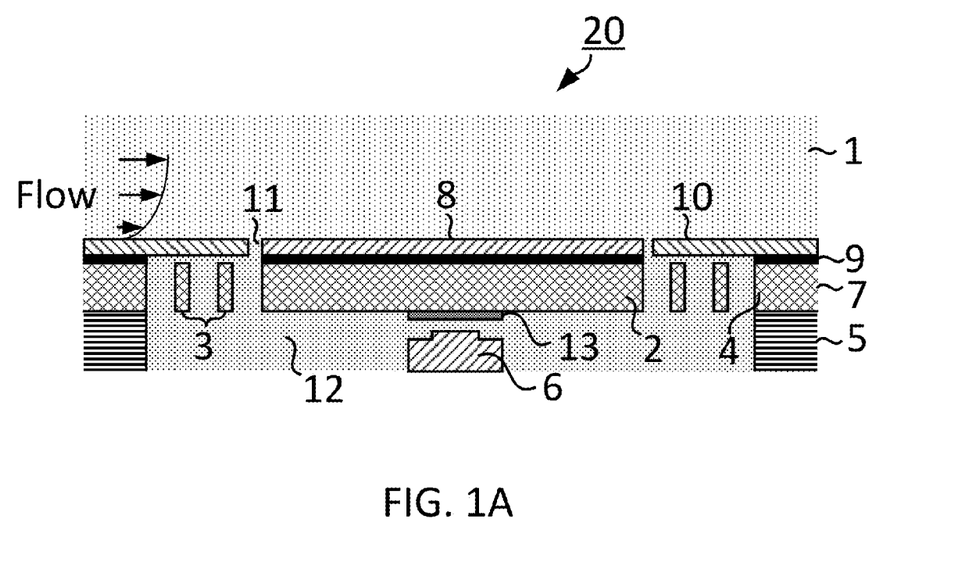
FIG. 1A illustrates a cross-sectional view of a schematic representation of a shear-sensing unit according to one embodiment. Note that FIG. 1A is not drawn to scale; middle plate (i.e., floating plate) is much larger in the in-plane direction in reality than it appears in FIG. 1A.

FIG. 1A shows a schematic cross-sectional view of the shear-sensing unit 20 in the presence of flowing fluid 1. The fluid 1 is a liquid (typically water) or a gas (typically air). As seen in FIG. 1A, the shear-sensing unit 20 includes a floating plate 2, flexure beams 3 which suspend the floating plate 2, and a frame plate 4 that are all fabricated monolithically from one piece of plate 7. The floating plate 2 is located in substantially the same plane as the frame plate 4. The flexure beams 3 are also located in substantially the same plane with the frame plate 4. The frame plate 4 is fixed on substrate 5. The substrate 5 may include a surface of an object that is to be tested. This may include, for example, the hull of a boat or an outer surface of an airplane. A sample surface 8 is attached on top of the floating plate 2. Optionally, an adhesive 9 may be used for the attachment of the sample surface 8 although other techniques may be employed such as, for example, direct bonding or removable fasteners (e.g., screws, bolts, clips, or the like). The frame plate 4 may be covered with surrounding surface 10 to make the top surface of the surrounding surface 10 substantially flush with the top surface of the sample surface 8. The surrounding surface 10 may overhang from the frame plate 4 over the flexure beams 3 as seen in FIG. 1A to minimize the surface gap 11 that is created between the sample surface 8 and the surrounding surface 10. A clearance is created between the overhang section of the surrounding surface 10 and the flexure beams 3 by, for example, the thickness of the adhesive 9.

Figure 1B:
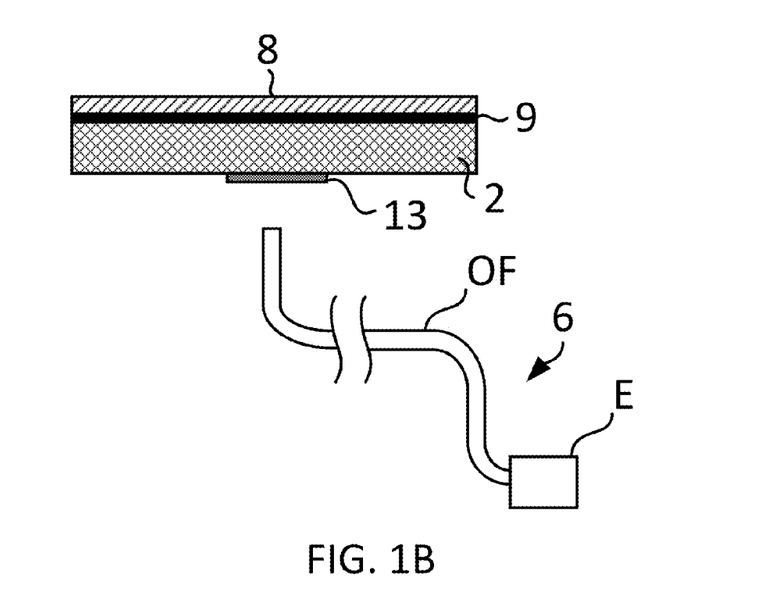
FIG. 1B schematically illustrates an embodiment where the displacement sensor includes an optical fiber and an optical encoder that is located remotely away from the floating plate.

During use, the space underneath the floating plate 2 is filled with fluid 12, which may be the same composition as the flowing fluid 1. A displacement sensor 6 is located on the back or underside of the floating plate 2 as seen in FIG. 1A. The displacement sensor 6 may have an encoder located inside of an isolated chamber or, alternatively, located away from the floating plate 2 located in a remote location. For example, the displacement sensor 6 may use an optical fiber (OF) whose one end faces an optical ruler 13 located underneath the floating plate 2 and the other end terminates at an optical encoder (E) located at a remote location as is seen, for example, in FIG. 1B. The displacement sensor 6 sends a signal out and receives the signal back from the ruler 13 that is attached to or formed on the back of the floating plate 2 to read the displacement of the floating plate 2. The ruler 13 may be secured to the back of the floating plate 2 using an adhesive or any other known method of bonding or mechanical fastening. The ruler 13 may also be formed directly (e.g., by thin-film deposition, etching into the surface) in the back surface of the floating plate 2. Compared with strain gauges widely used for shear sensors, the use of displacement sensor 6 is more advantageous by allowing other different methods. For example, an optical encoder is preferable because it is insensitive to temperature and pressure variations and can be used at high temperatures if an optical fiber (OF) is used (i.e., the encoder (E) is located externally or remote from the sensing unit 20). Compared with capacitance-based sensing, the optical method using an optical encoder is immune to electromagnetic interference and can be applied to a wide variety of fluids since the displacement sensor 6 may be easily sealed or potted in an isolated chamber.

Figure 1C:
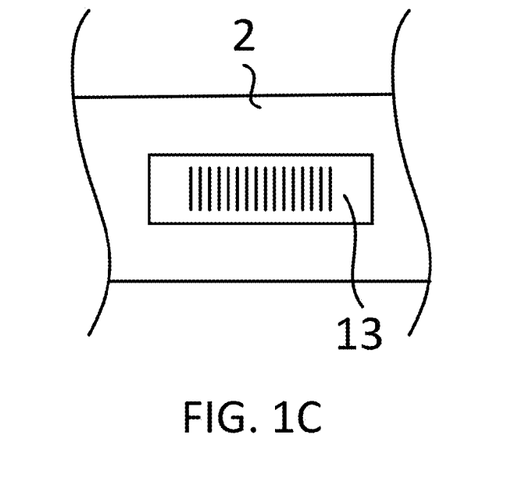
FIG. 1C illustrates a facing view of the ruler that is secured to or formed on the back of the floating plate.
Figure 1D:
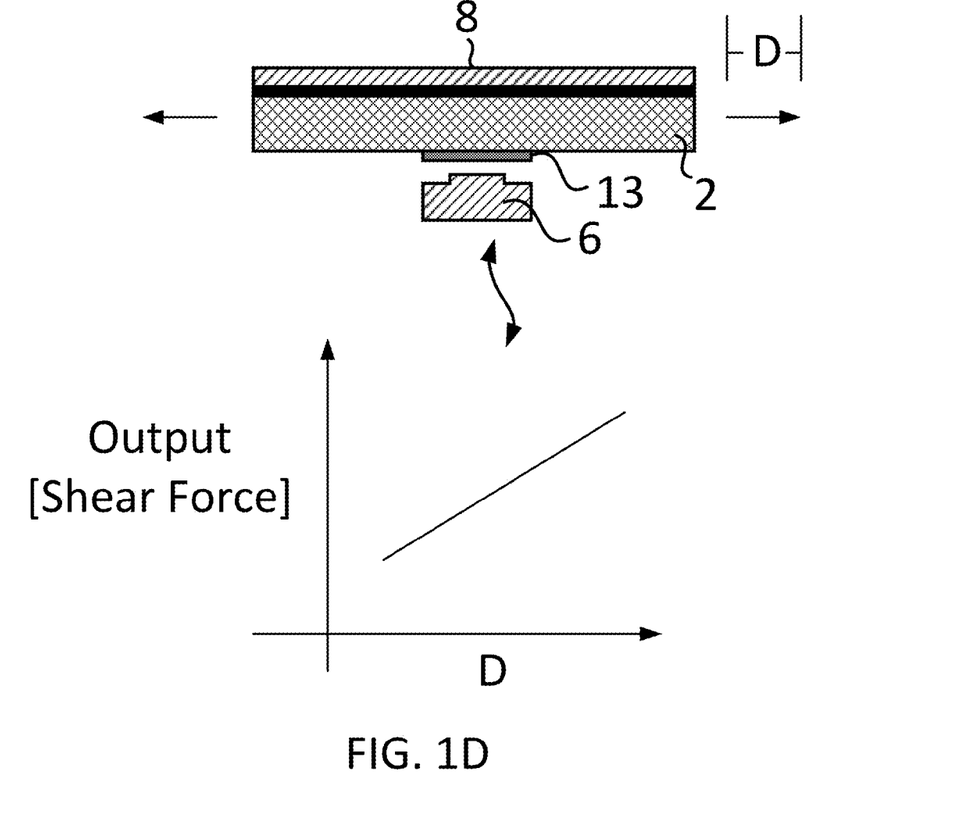
FIG. 1D illustrates schematically how the displacement sensor generates an output signal as a function of distance (D) that is used to measure the shear force that is experienced by the sample surface that is affixed to the floating plate.

FIG. 1C illustrates a facing view of the ruler 13 that is secured to or formed on the back of the floating plate 2. The ruler 13 includes graduations that are used by the displacement sensor 6 to measure the degree of in-plane movement of the floating plate 2. For example, in the embodiment where the ruler 13 is an optical ruler, the graduations may include diffraction gratings that are used by the optical encoding functionality of the displacement sensor 6 to quantify the degree of in-plane movement of the floating plate 2. FIG. 1D illustrates schematically how the displacement sensor 6 generates an output signal as a function of distance (D) that is used to measure the shear force that is experienced by the sample surface 8 that is affixed to the floating plate 2. Typically, in the range of flow rates to be tested, the output signal has a generally linear relationship to the displacement distance (D) that is measured. The use of the floating plate 2 in combination with the optical-based ruler 13 for detecting in-plane movement was confirmed enabling the shear-sensing unit 20 to measure changes in shear forces that are smaller than 100 μN.

Figure 2A:
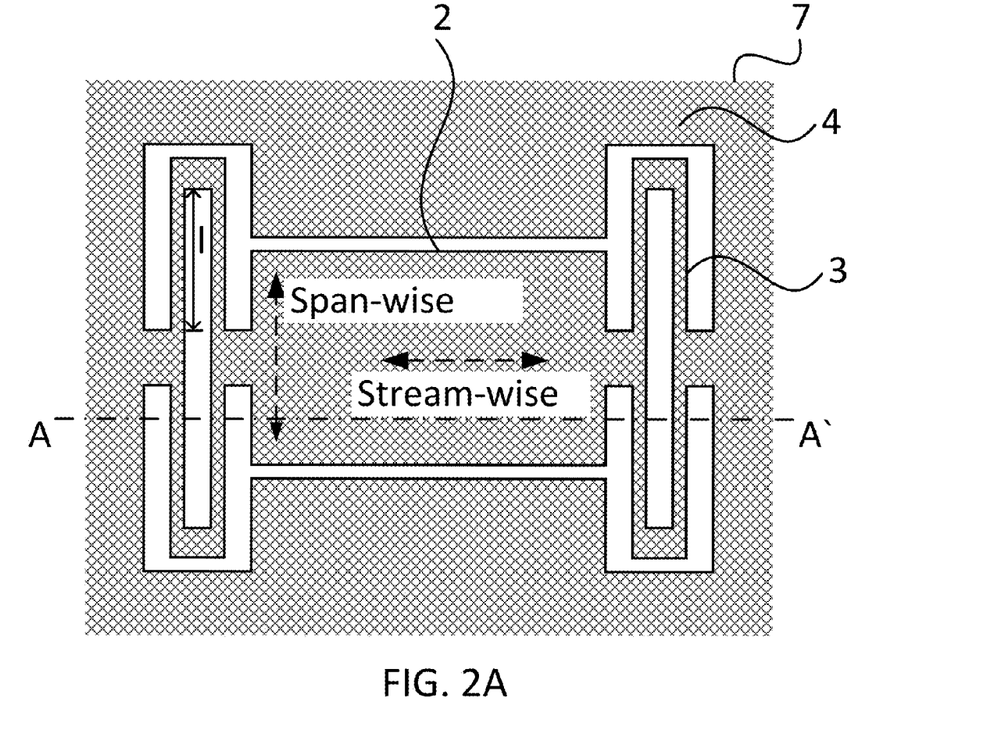
Figure 2B:
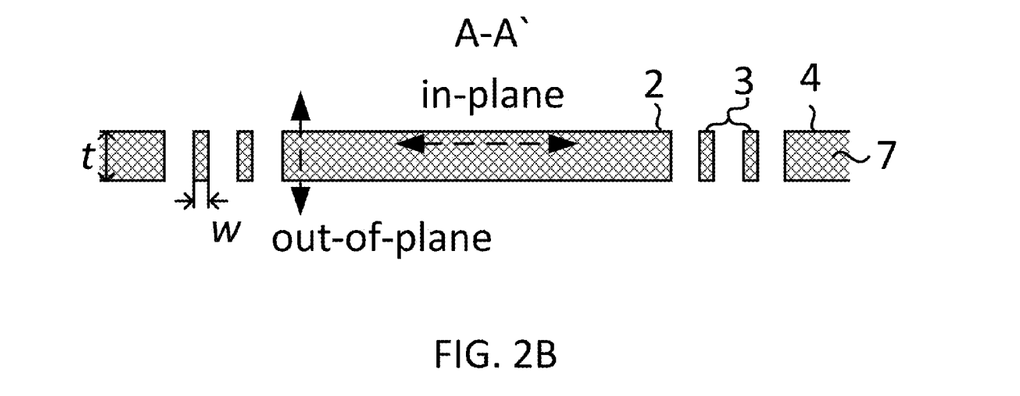
Figure 2C:
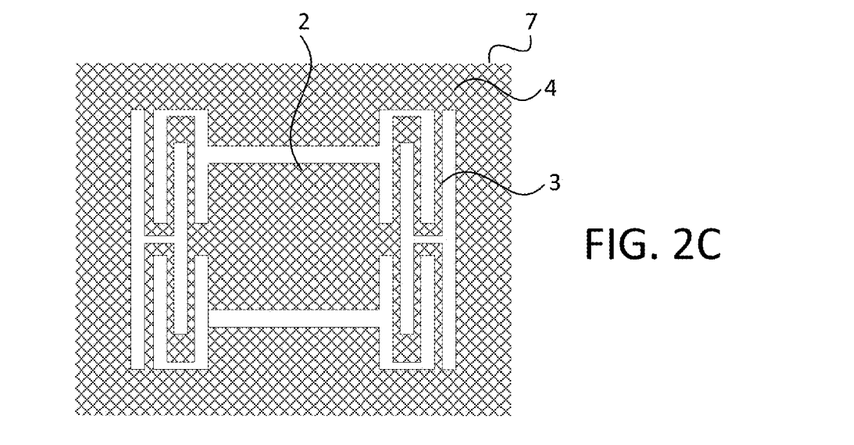
FIG. 2C illustrates a top view of a schematic representation of a shear sensing unit having flexure beams in the shape of a double-folded beam (i.e., three straight sections).
Figure 2D:
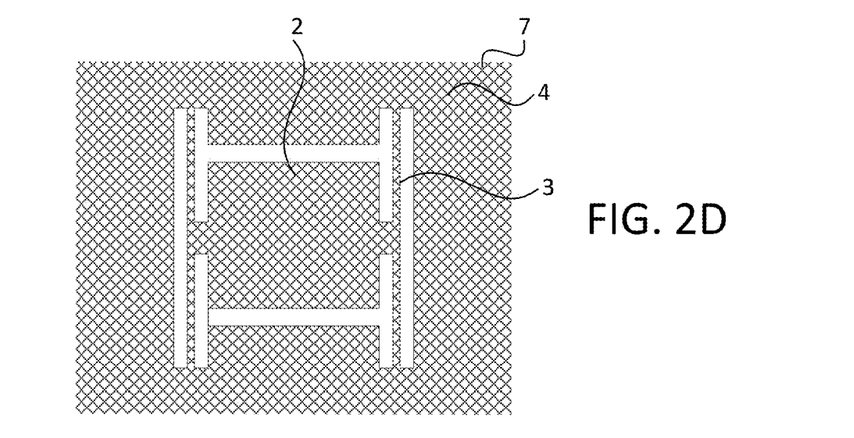
FIG. 2D illustrates a top view of a schematic representation of a shear sensing unit having an unfolded flexure beam (i.e., one straight section).
Figure 2E:
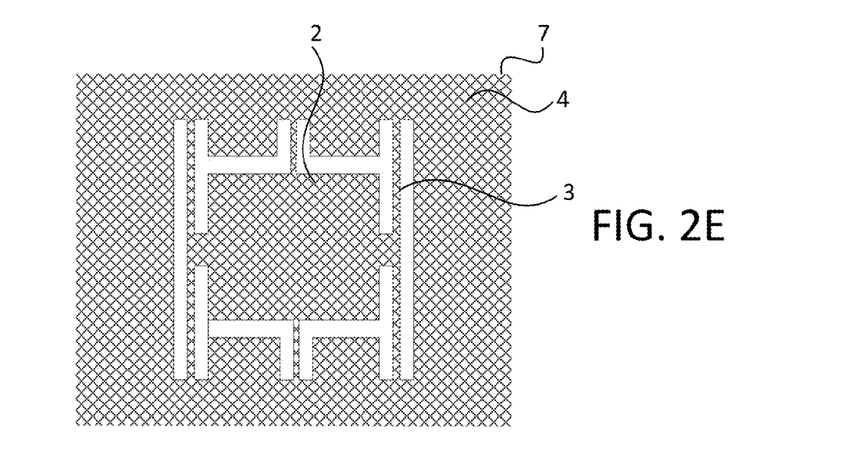
FIG. 2E illustrates a top view of a schematic representation of a shear sensing unit having six (6) flexure beams

FIG. 2A and FIG. 2B show the schematic top view and cross-section view, respectively, of the shear-sensing unit 20 in one embodiment. As shown in FIG. 2A, the floating plate 2 is suspended from the frame plate 4 by four (4) flexure beams 3 each having a shape of single-folded beam (i.e., each flexure beam 3 has two straight sections). FIGS. 2A and 2B are presented simply as one illustrative design. The flexure beams 3 are shaped to deform or flex along the plane of the floating plate 2. For example, the flexure beams 3 may have a shape of double-folded beam (thus three straight sections) as shown in FIG. 2C or unfolded beam (thus one straight section as usual) as shown in FIG. 2D. Also, six (6) flexure beams 3 may be employed, as illustrated in FIG. 2E, if desired instead of the four (4) flexure beams 3 illustrated in FIGS. 2A, 2C, and 2D. The shear force exerted on the sample surface 8 displaces the floating plate 2 in the in-plane direction (e.g., laterally) in the stream-wise direction against the restoring force exerted by the flexure beams 3. The restoring force (F) of the flexure beams 3 follows Hook's law:

$$F = k_{in\text{-}plane} \cdot \Delta x = \frac{12NEI}{nl^3} \cdot \Delta x \qquad \text{Eq. 1}$$

where $k_{in\text{-}plane}$ is the spring constant of the flexure beams 3, $\Delta x$ is the displacement of the floating plate 2, N is the number of flexure beams 3 (i.e., four (4) in FIGS. 2A, 2C, and 2D) suspending the floating plate 2, n is number of straight sections in each flexure beam (i.e., two in FIG. 2A, three in FIG. 2C, and one in FIG. 2D), E is the Young's modulus of the beam material, and I is moment of inertia of the straight section of the flexure beams bending in the in-plane direction, l is the length of each straight section (indicated in FIG. 2A) of the flexure beams 3. The total length of the beams is nl. With low spring constant flexure beams and a high resolution optical encoder (e.g., 2 nm), the flexure beams 3 can be designed to permit shear force measurement of a very high resolution.

Because the sensing unit 20 is designed to measure the shear force only in the stream-wise direction, the flexure beam 3 should be stiff in all the other directions. The stiffness on the span-wise direction is high since this direction is along the beam length. In order to increase the stiffness in out-of-plane direction (i.e., normal to the in-plane direction), the thickness (t) (FIG. 2B) of the flexure beams 3 is designed to be larger or often much larger (e.g., ten times) than the width (w) of each of the flexure beams 3. This design makes the spring constant in the out-of-plane direction much larger or at least larger than that in-plane or stream-wise direction. For example, assuming beams of rectangular cross section, the ratio of spring constants in the out-of-plane direction to that in stream-wise direction is:

$$\frac{k_{in\text{-}plane}}{k_{out\text{-}of\text{-}plane}} = \frac{I_{in\text{-}plane}}{I_{out\text{-}of\text{-}plane}} = \left(\frac{t}{w}\right)^2 \qquad \text{Eq. 2}$$

In order to achieve high sensitivity (i.e., low spring constant in the stream-wise direction) but high stiffness in the out-of-plane direction, the beam width (w) needs to be small, for example, less than 1 mm (e.g., ~0.25 mm), but the beam length (l) needs to be large (at least fifty (50) times larger than the width) (e.g., ~50 mm) and the beam thickness (t) needs to be larger than the width (e.g., ~10 mm). This requirement is so challenging in practice and considered impossible to machine with metals. Considering fabrication methods, MEMS technology is excluded here since the floating plate 2 here has a wide range of sizes (e.g., several millimeters to tens of centimeters) to allow mounting of different sample surfaces and accepting different testing applications. Also, MEMS technology usually uses silicon, which is too brittle for repeated sample replacements (i.e., attachment and detachment of sample surfaces 8), and MEMS sensors are usually not robust against water or particle impingement common in flow tests especially field tests. Other non-monolithic shear stress sensors (e.g., single pivot design, which uses metals and is robust) are also excluded in this discussion since the assembly increases the chances of misalignments and the cost.

In one embodiment, the shear-sensing unit 20 measures the shear force that is imparted on sample surfaces 8 by measuring the displacement (D or $\Delta x$ term in Equation 1 above) and using Eq. 1 to calculate the measured shear force. This may be accomplished using a processor or computing device that automatically calculates the measured force using Equation 1 above. For example, software or instructions that are executed by the processor or computing device may automatically calculate the measured shear force using the measured displacement values that is output by the shear-sensing unit 20. Rather than calculating the measured force using Equation 1, a look-up table or graph may be provided that can correlate measured displacement to measured force. In yet another alternative, a calibration curve for the shear-sensing unit 20 that was generated using applied (known) forces may be used to translate or convert measured displacement readings to measured shear force values. This may be implemented using a processor or other computing device.

The sensing unit 20 can be fabricated out of a monolithic substrate using wire electrical discharge machining (EDM) to fabricate long beams having a high-aspect-ratio (i.e., thick and narrow) (e.g., 10) cross section with feature sizes below a millimeter (e.g., 0.25 mm) and resolutions in microns. The wire EDM can also fabricate a floating plate 2 of different sizes suspended by the flexure beams 3. However, using the current state of the art machining techniques, such highly flexible beams would undergo non-negligible amounts of deflection during wire EDM due to thermal stress, dielectric liquid flushing, mechanical vibration, etc., causing non-uniform beam width or broken beams. Similar challenges are expected for other slit-cutting methods other than the wide EDM, such as waterjet cutting and laser machining.

Figure 3A:
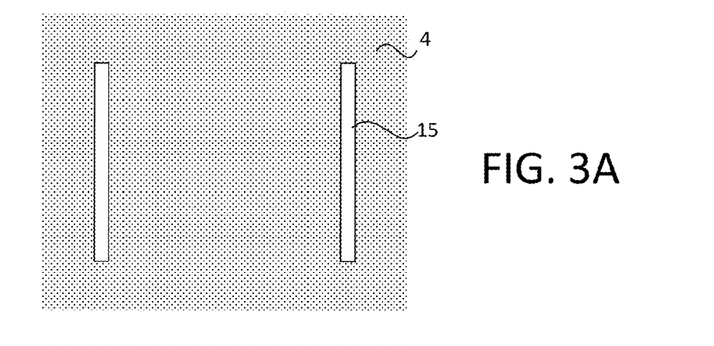
FIGS. 3A-3D illustrate an exemplary process to machine the floating plate and suspending beams of a shear-sensing unit.
Figure 3B:
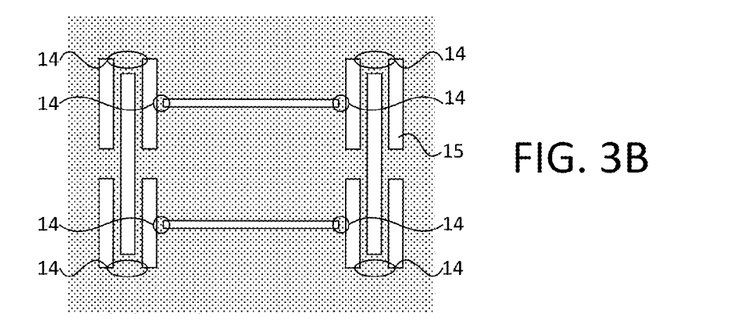
Figure 3C:
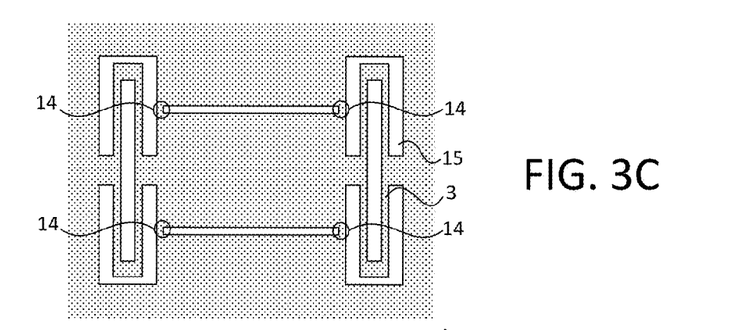
Figure 3D:
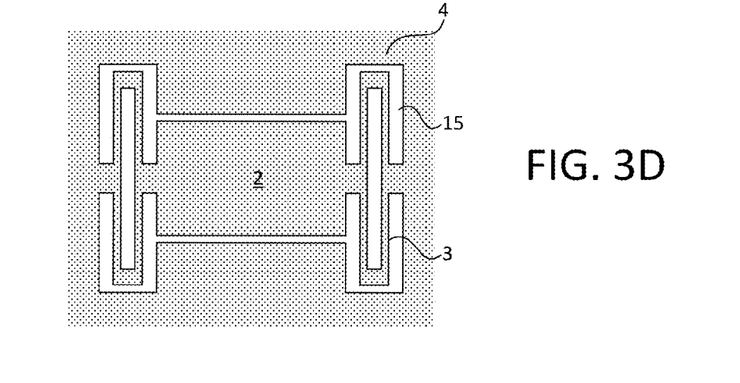
Figure 3E:
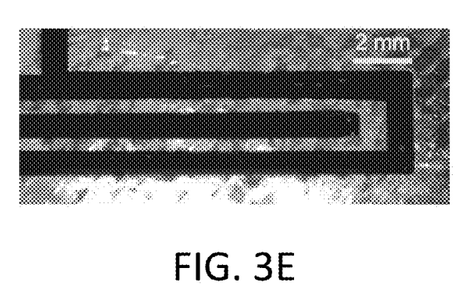
FIG. 3E illustrates a photographic image of a successful attempt to manufacture flexure beams suspending the floating plate when wire EDM cutting followed the specific paths and sequence illustrated in FIGS. 3A-3D.

In order to solve this problem, a specially designed cutting path and sequence using the temporary connections can be used. This machining concept is composed of three steps: (1) while defining the flexure beams 3 and floating plate 2 make cuts except for some strategic locations to leave temporary connections; (2) release the flexure beams 3 by cutting the relevant temporary connections; (3) release the floating plate 2 by cutting the remaining temporary connections. FIGS. 3A-3D illustrate one example of cutting paths and sequences with wire EDM that use temporary connections to obtain the sensing unit 20 of FIGS. 2A and 2B. As seen in FIGS. 3A and 3B, individual cuts 15 are sequentially made to define parts of the designed flexure beams 3 and the floating plate 2. However, these cuts 15 are isolated (not yet connected to each other) so all the flexure beams 3 and the floating plate 2 are still fixed to the frame plate 4 by temporary connections 14. In FIG. 3C, some of the isolated cuts 15 are connected to form the folded shape of the flexure beams 3. These short cutting actions in the rigid directions (to connect neighboring isolated cuts 15) to remove the temporary connections 14 do not deflect the beams being formed and do not affect the integrity of the eventual flexure beams 3, while releasing very flexible beams (e.g., single-folded beams shown). For the releasing steps, other types of temporary support (e.g., wax filling the gaps) could also be used. In FIG. 3D, the floating plate 2 is released at the four corners, completing the machining process of the plate 7. It is also possible to leave other locations for the temporary connections for the same design of flexure beams 3 and floating plate 2. Different designs of floating plate and flexure beams would require different temporary connections, but following a similar process concept of leaving temporary connections 14 that are later removed. The utility of a cutting path and sequence that leave temporary connections and that are removed later, near the end of the process have been proven with wire EDM, as seen in FIG. 3E. Adoption of a well-designed cutting path and sequence increase the chance to succeed when the desired shaped is challenging to machine (e.g., very flexible beams, large floating plate). This type of specific cutting path and sequence may also be applied to other slit cutting machining methods, such as waterjet cutting, when one needs to carve out extremely long and slender members.

Figure 4:
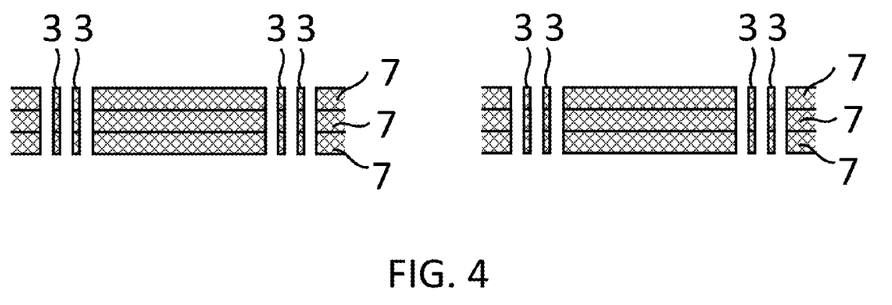
FIG. 4 illustrates a cross-sectional view of multiple plates that are stacked together and cut substantially simultaneously using wire EDM or another slit cutting machining method, producing multiple sensing unit plates in one cutting process.

To reduce the machining cost per unit, one can machine multiple sensor plates 7 at the same time. As shown in FIG. 4, multiple sensor plates 7 are stacked together, and the flexure beams 3 are cut at substantially the same time using wire EDM or other slit cutting machining methods. Furthermore, multiple sensing plates 7 can be machined from one large plate at the same time, using multiple tools operating at the same time. Shown in FIG. 4 is a stack of three plates 7 machined at two locations at the same time to create six (6) sensing plates 7 in one machining process.

Since the shear-sensing unit 20 is often used in a harsh environment, an effort may be made to address this challenge. To function in a corrosive environment, the plate 7 can be made of a non-corrosive material, such as stainless steel, titanium, or even a polymer. Alternatively, the plate 7 may be coated with a thin layer of a non-corrosive material after the plate 7 is machined. To function in a high-temperature environment, the plate 7 can be made of a refractory material, such as tungsten or even a ceramic.

While slit cutting methods are considered to machine the plate 7 from a metal, other machining methods can be adopted, such as high-precision casting and injection molding, processes that are typically desired for large volume production.

Figure 5A:
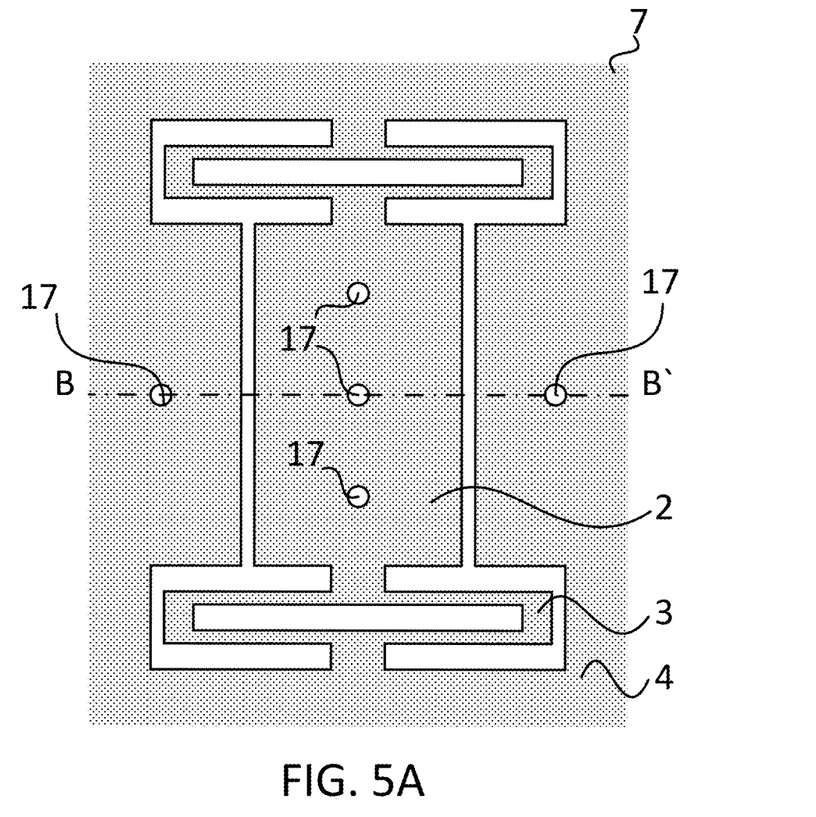
FIG. 5A illustrates a top view of a schematic representation of one embodiment used to temporarily immobilize the floating plate.
Figure 5B:
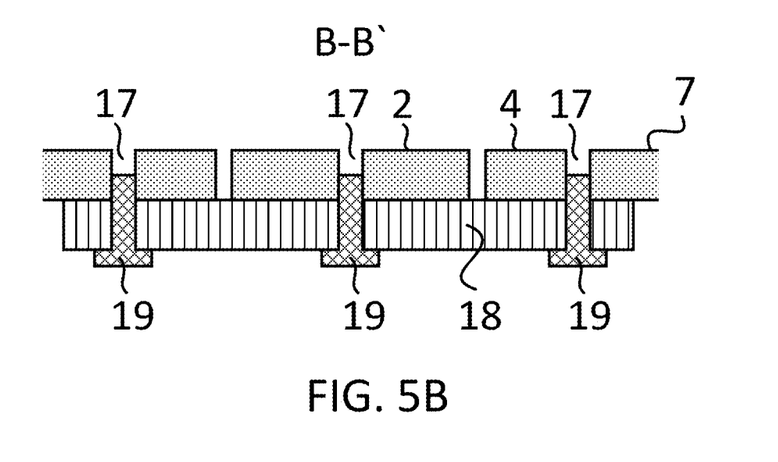
FIG. 5B illustrates a cross-sectional view of a schematic representation of one embodiment used to temporarily immobilize the floating plate taken along the line B-B' of FIG. 5A.

During attachment and detachment of sample surfaces 8 or shipping of the sensing unit 20, immobilization of the floating plate 2 helps preventing potential damage to the beams 3 caused by accidental impacts. FIGS. 5A and 5B show one approach to immobilize the floating plate 2. In this embodiment, holes 17 (which may be threaded) are formed in the floating plate 2 and frame plate 4 before the EDM (or other cutting) process, as shown in FIG. 5A. The floating plate 2 and frame plate 4 are then attached to a fixture plate 18 by one or more fasteners 19 (e.g., screws) as shown in FIG. 5B. The floating plate 2 can thus easily be temporarily immobilized relative to the frame plate 4 using the fixture plate 18. The fixture plate 18 can be removed by removing the fasteners 19 prior to using the sensing unit 20.

Figure 6:
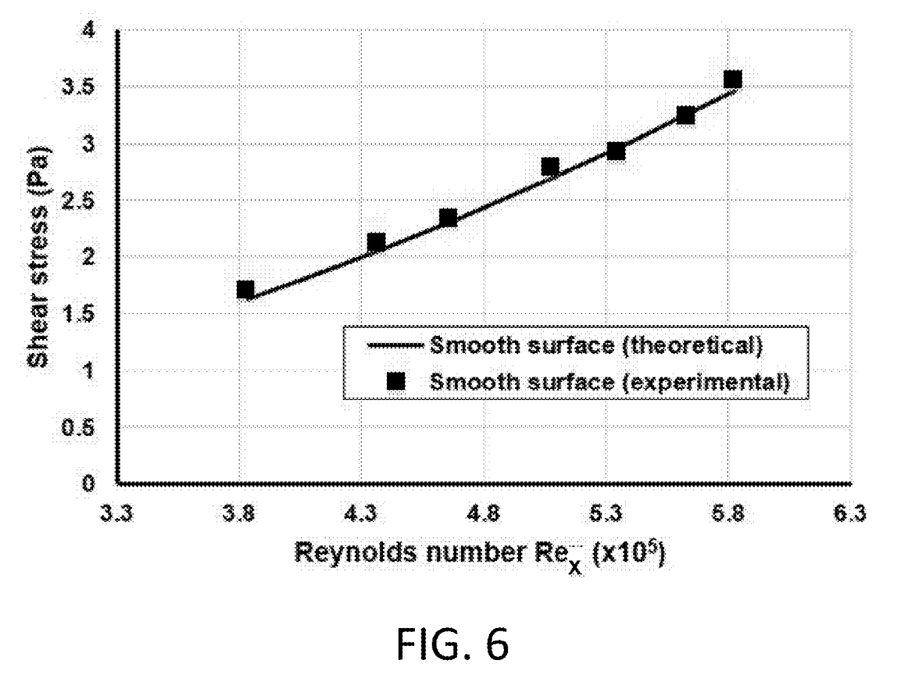
FIG. 6 shows the testing results of a shear-sensing unit in water tunnel at different Reynolds numbers ($Re_x$), indicating high resolution and accuracy.

The shear-sensing unit 20 was successfully manufactured as described herein and tested in a water tunnel subject to turbulent flows. In one embodiment, a piece of bare silicon was used as sample surface 8 and a commercial Talbot-effect-based optical encoder (e.g., Mercury 2000, MicroE Encoder, GSI group, Bedford, Mass.) was used as the displacement sensor 6. The encoder output was first zeroed in static conditions as 0 and then recorded after flow is introduced. The average output of the encoder during flow was then calculated and transformed into displacement value based on the interpolation setting of the optical encoder. Then the shear stress value was obtained by multiplying the displacement by the spring constant of the beams 3. One exemplary shear measurement obtained using the shear-sensing unit 20 is shown in FIG. 6. The theoretical curve was obtained from the empirical curve of H. Schlichting, "Boundary-layer theory", pp. 638-639 (McGraw-Hill, 1979), which is incorporated herein by reference, to confirm the performance of the unit. The results showed good accuracy and high resolution not possible before.

While embodiments of the present invention have been shown and described, various modifications may be made without departing from the scope of the present invention. The invention, therefore, should not be limited except to the following claims and their equivalents.

What is claimed is:

1. A shear-sensing unit comprising:
   a frame plate;
   a floating plate disposed inside the frame plate in substantially the same plane with the frame plate and secured to the frame plate only via a plurality of flexure beams disposed in substantially the same plane with the frame plate, the floating plate being free of any actuator imparting force to the floating plate against the frame plate and having a sample supporting surface and a back surface;
   a ruler secured to or formed on the back surface of the floating plate;
   a displacement sensor configured to sense in-plane movement of the ruler; and
   wherein the plurality of flexure beams are shaped to deform in a direction along a plane of the floating plate and wherein each of the plurality of flexure beams has a width smaller than 1 mm, a thickness larger than the width, and total length at least fifty (50) times larger than the width.

2. The shear-sensing unit of claim 1, wherein the measurement resolution is smaller than 100 μN.

3. The shear-sensing unit of claim 1, wherein the plurality of flexure beams comprises at least four (4) flexure beams.

4. The shear-sensing unit of claim 1, wherein each of the plurality of flexure beams has at least one fold.

5. The shear-sensing unit of claim 1, further comprising a sample on the sample supporting surface of the floating plate.

6. The shear-sensing unit of claim 5, wherein the sample is secured to the sample supporting surface of the floating plate with an adhesive, by direct bonding, or by a fastener.

7. The shear-sensing unit of claim 1, wherein the frame plate and floating plate are made of a non-corrosive material.

8. The shear-sensing unit of claim 1, wherein the frame plate and floating plate are coated with a layer of non-corrosive material.

9. The shear-sensing unit of claim 5, further comprising a surrounding surface adhered to the frame plate and separated from the sample on the floating plate by a gap.

10. The shear-sensing unit of claim 1, further comprising a fluid interposed between the floating plate and the displacement sensor.

11. The shear-sensing unit of claim 1, further comprising a temporary fixture plate secured to the floating plate and the frame plate.

12. The shear-sensing unit of claim 11, wherein the fixture plate is secured to the floating plate and the frame plate with one or more fasteners.

13. The shear-sensing unit of claim 1, wherein the ruler is an optical ruler and the displacement sensor comprises an optical encoder.

14. The shear-sensing unit of claim 13, wherein the optical encoder comprises an encoder unit coupled to an optical fiber, wherein another end of the optical fiber is disposed adjacent to the optical ruler.

15. The shear-sensing unit of claim 1, wherein the displacement sensor outputs a signal that indicates the distance (D) of in-plane movement of the floating plate.

16. A method of making the shear-sensing unit of claim 1 comprising:
   providing at least one plate and using a slit-cutting method to define the flexure beams and the floating plate wherein respective temporary connections are formed for the flexure beams and the floating plate;
   removing any temporary connection(s) located adjacent to the flexure beams to complete defining the flexure beams; and
   removing any temporary connection(s) located adjacent to the floating plate to complete defining the floating plate.

17. The method of claim 16, wherein the slit-cutting method is wire electrical discharge machining (EDM).

18. The method of claim 16, wherein the temporary connections are formed by saving respective portions of the provided plate from being removed by the slit-cutting method.

19. The method of claim 16, wherein multiple plates are stacked and machined simultaneously by a slit-cutting method.

20. A method of using the shear-sensing unit of claim 1, comprising:
   mounting a sample on the sample supporting surface of the floating plate;
   subjecting the sample on the shear-sensing unit to fluid flow over the sample;
   measuring the displacement of the ruler; and
   converting the measured displacement to a measured shear force.

21. The method of claim 20, wherein the shear-sensing unit has a force measurement resolution smaller than 100 μN.

* * * * *